US006255421B1

(12) United States Patent
Plochocka et al.

(10) Patent No.: US 6,255,421 B1
(45) Date of Patent: *Jul. 3, 2001

(54) NON-AQUEOUS, HETEROGENEOUS POLYMERIZATION PROCESS AND REACTION PRODUCT OBTAINED THEREBY

(75) Inventors: Krystyna Plochocka, Scotch Plains; Jui-Chang Chuang, Wayne; Jenn S. Shih, Paramus, all of NJ (US)

(73) Assignee: ISP Investments Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/988,121

(22) Filed: Dec. 10, 1997

(51) Int. Cl.$^7$ ........................................... C08F 2/12
(52) U.S. Cl. .................. 526/194; 526/219.6; 526/230.5; 526/232.1; 526/227; 526/263; 526/264; 526/333; 526/334
(58) Field of Search ....................................... 526/194, 263, 526/264, 333, 334, 219.6, 227, 232.1, 230.5

(56) References Cited

FOREIGN PATENT DOCUMENTS 1 283 327 * 7/1972 (GB) .

* cited by examiner

Primary Examiner—Fred Zitomer
(74) Attorney, Agent, or Firm—Walter Katz; William J. Davis; Marilyn J. Maue

(57) ABSTRACT

A non-aqueous, heterogeneous polymerization process comprises heating a reaction mixture of about 5–70%, preferably 10–30%, by weight, of a vinyl monomer in an oil as solvent, and a free radical initiator, optionally in the presence of a crosslinking agent and/or a surfactant, wherein the oil solvent is present in an amount sufficient to keep the resultant polymer in a stirrable state throughout the polymerization. The polymer reaction product is capable of forming a uniform emulsion or gel upon addition of water thereto.

8 Claims, No Drawings

NON-AQUEOUS, HETEROGENEOUS POLYMERIZATION PROCESS AND REACTION PRODUCT OBTAINED THEREBY

BACKGROUND OF THE INVENTION

1. Field of the Invention

This invention relates to a polymerization process, and more particularly, to non-aqueous, heterogeneous polymerization of a vinyl monomer in oil as a solvent.

2. Description of the Prior Art

J. Shih, in U.S. Pat. No. 5,015,708, described a non-aqueous, precipitation polymerization process for making N-vinyllactam terpolymers in which the polymerization step was carried out in an aliphatic hydrocarbon solvent such as heptane or hexane. The reaction product was a white powder of the terpolymer, however, with undesirable traces of heptane or hexane present therein.

S. Kopolow, in U.S. Pat. No. 5,130,121, disclosed an aqueous polymerization process for making a N-vinylpyrrolidone polymer encapsulating a silicone oil.

Accordingly, it is desired to provide a non-aqueous, heterogeneous polymerization process for making vinyl polymers using an oil solvent, whose presence both during the polymerization and in the reaction product is advantageous for commercial use of the vinyl polymer, particularly in cosmetic compositions.

These and other objects and features of the invention will be made apparent from the following description of the invention.

SUMMARY OF THE INVENTION

What is described herein is a non-aqueous, heterogeneous polymerization process for making vinyl polymers. The process comprises heating a reaction mixture of, by weight, about 5–70%, preferably 10–30% of a vinyl monomer in an oil as solvent, and a free radical initiator, optionally in the presence of a crosslinking agent and/or a surfactant, wherein the oil solvent is present in an amount sufficient to keep the resultant polymer in a stirrable state throughout the polymerization. The polymer reaction product obtained thereby is capable of forming a uniform emulsion or gel upon addition of water thereto.

DETAILED DESCRIPTION OF THE INVENTION

The unique properties of many oils make it desirable to include them in aqueous-based compositions. For example, cosmetically and pharmaceutically-acceptable materials such as silicone oils, fluids and gums, mineral oils, and water-insoluble organic esters such as isopropyl palmitate and isopropyl myristate, are particularly useful in formulations for the hair and skin. In these compositions, the lubricity and hydrophobicity properties of the oils are beneficial for the user.

In this invention, vinyl polymers useful in cosmetic compositions are prepared in a non-aqueous, heterogeneous polymerization process using an oil as a solvent for the monomer during the polymerization reaction. The oil solvent also acts as a medium to keep the polymer product in a stirrable state throughout the polymerization. The reaction product is a slurry of the vinyl polymer in oil. If desired, the reaction product may be filtered to provide the vinyl polymer as a powder swollen with oil. Thereafter, the reaction product itself, or the polymer powder swollen with oil, may be homogenized with water to form a uniform liquid emulsion or gel which is directly useful as the cosmetic or pharmaceutical composition.

Generally about 5–70%, preferably 10–30%, by weight, of the vinyl monomer reactant is used in the process, and about 30–95% of the oil is included for the solvent and medium functions in the process.

Suitable silicone oils or fluids for use in the invention may be selected from non-volatile silicones, such as polyalkyl siloxanes, polyaryl siloxanes, polyalkylaryl siloxanes and polyether siloxane copolymers; and volatile silicones such as cyclomethicones also may be used.

Non-volatile polyalkylsiloxanes thus include, for example, polydimethylsiloxanes (Dimethicone) with viscosities ranging from about 5 to about 600,000 centistokes (cS) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cS, and most preferably, a viscosity of up to about 15,000 cS.

Suitable non-volatile polyalkylaryl siloxanes include, for example, poly(methylphenyl) siloxanes having viscosities of about 15 to 65 cS at 25° C. These siloxanes are available, for example, from the General Electric as SF 1075 methylphenyl fluid or from Dow Corning as 556 Cosmetic Grade Fluid. Additionally, poly(dimethylsiloxane)-(diphenylsiloxane) copolymers having a viscosity in the range of about 10 to 100,000 cS at 25° C. are useful.

These and other suitable silicones are disclosed in U.S. Pat. Nos. 2,826,551, 3,964,500 and 4,364,837.

Other suitable oils for use herein include cosmetically or pharmaceutically-acceptable materials such as light and heavy mineral oils, and water-insoluble organic esters such as isopropyl palmitate and isopropyl myristate.

The polymerization process is carried out with a free radical initiator present in the polymerization reaction mixture. The reaction product thus includes the vinyl polymer corresponding to the vinyl monomer or monomers selected. Suitable free radical initiators are diacetyl peroxide, dibenzoyl peroxide, dilauroyl peroxide, t-butyl peroxypivalate, t-butyl peroctoate, t-amyl peroxypivalate, t-butyl peroxy-2-ethylhexanoate, di-(4-t-butylcyclohexyl)peroxydicarbonate, 2,2'-azobis(isobutyronitrile), 2,2'-azo-bis(2,4-dimethylvaleronitrile), or 1,1'-azo-bis(cyanocyclohexane), and mixtures thereof.

A crosslinked vinyl polymer may be obtained in the process when the optional crosslinking agent is included in the reaction mixture. Suitably, the crosslinking agent is present in an amount of about 0.1–10 wt. %, preferably 0.3–2%, based on the amount of vinyl monomer present. In the presence of such a crosslinking agent, the vinyl monomer will form the corresponding crosslinked vinyl polymer, which, upon homogenization with water, will provide a uniform liquid gel product.

In the practice of the present invention, the oil solvent is charged into a reactor, under agitation, and in a nitrogen atmosphere, and heated to about 40–150° C., preferably about 65° C. Then the free radical initiator is added. Thereafter the vinyl monomer is added continuously over a period of about 1–12 hours, preferably about 3–6 hours. Preferably, the vinyl monomer and optional crosslinking agent are fed into the reactor at a rate such that substantially no free monomer is present during the polymerization.

After polymerization is complete, the polymer is obtained as a slurry in oil. The slurry can be used as is or filtered to remove excess oil where the product consists of solid polymer with significant amount of absorbed oil. Both slurry and filtered polymer are useful in cosmetic and pharmaceutical formulations.

Suitable vinyl monomers include, but are not limited to, N-vinylamides and N-vinyllactams, such as N-vinylpyrrolidone, N-vinylcaprolactam; and N-vinylformamide, and optinally with comonomers such as vinyl acetate, acrylic acid, methacrylic acid, acrylamide, methacrylamide, an alkyl (meth)acrylate, an alkyl (meth) acrylamide, a hydroxyalkyl (meth)acrylate and a hydroxyalkyl (meth)acrylamide, and a N,N-dialkylamino-alkyl (meth)acrylate wherein alkyl is independently a $C_1$ to $C_4$ alkyl group and N,N-dialkylaminoalkyl methacrylamide (alkyl being as defined before), and their quaternary derivatives; and mixtures thereof.

Suitable crosslinking agents include, but are not limited to, diallylimidazolidone, divinyl ether of diethylene glycol, pentaerythritol triallyl ether (PETA); triallyl-1,3,5-triazine-2,4,6-(1H,3H,5H)trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis(methacrylamide), methylene-bis (acrylamide), N,N-divinylimidazolidone, ethylidene-bis(N-vinylpyrrolidone) (EBVP), hexaallyl sucrose, or bis(N,N-acrylamide).

Another optional component of the reaction mixture is a surfactant. The presence of a surfactant will function to effectively stabilize the desired emulsion and gel products. Generally, an oil soluble surfactant is present in the reaction mixture and a water soluble surfactant during the water homogenization, in an amount of about 0.5–10%, preferably 1–5%, based on oil present. Suitable oil soluble surfactants useful for polymerization include, but are not limited to, cetyl dimethicone copolyol (Abil® EM-90, product of Goldschmidt Chemical Corp.); Span® 80 (ICI) and Dow Corning 3225 silicone.

The products made herein may be easily converted into emulsions or emulsified hydrogels which contain the polymer (linear or crosslinked) in the aqueous phase. The oil phase consists of the oil used during polymerization. The emulsions can be a water-in-oil (w/o), oil-in-water (o/w), or mixed type (w/o/w). When the polymer is crosslinked, the aqueous phase has attributes of a swollen crosslinked hydrogel. The hydrogel phase can be either dispersed in oil as fine gel particles (w/o), or the oil droplets can be dispersed in a continuous hydrogel phase (o/w).

The selected ratios of oil-to-water in such emulsions and emulsified hydrogels are predetermined by the desired use compositions; these can be adjusted within a broad range. Typically, oil-to-water ratios reside in the range of about 30:70 to about 10:90 by volume in the case of o/w emulsions and emulsified hydrogels. In corresponding w/o systems, the ratios of oil-to-water are suitably in the range of about 90:10 to about 30:70 by volume. Typically, when there is a need for a significant amount of oil in the final emulsion, the reaction product, that is, the slurry of polymer in oil, is directly converted into an emulsion or an emulsified hydrogel by addition of a calculated amount of water. When, however, the ratio of oil-to-water in the emulsion is desired to be low, the emulsion is made using the filtered reaction product that consists of polymer powder swollen with the absorbed oil.

When an o/w system is desired, the reaction product is gradually added to water, whereas when a w/o system is desired, water is added gradually to the reaction product, with appropriate rapid agitation or homogenization. Suitable surfactants should be added to these systems, such as, for example, Tween® 20, 21, 40, 61 (ICI) or Igepal® CO-630 (product of Rhone-Poulenc), for o/w emulsions and emulsified hydrogels; and Span® 60, 65, 80, 85 (ICI) for w/o systems. The surfactant added optionally to the polymerization reaction mixture also may be sufficient to form the desired emulsion or emulsified hydrogel.

The invention will now be described in further detail with reference to the following working examples.

EXAMPLE 1

A reaction mixture of 106.25 g of poly(dimethylsiloxane) silicone oil (Dow Corning 200® Fluid), having a Brookfield viscosity of 130 cS, was charged into a 1-liter glass resin kettle and heated to 65° C., while sparging with nitrogen. Then 0.05 g of t-butyl peroxypivalate (Lupersol® 11, 75% active, Elf Atochem), was added. Thereafter 18.75 g of N-vinylpyrrolidone (VP) monomer was continuously fed into the reactor over a period of 3 hours. Then a booster shot of 0.05 g Lupersol® 11 was added and the reaction was continued for another 2 hours. Still another booster of 0.05 g Lupersol® 11 was added and the reaction was continued for another 1 hour. The reaction mixture changed from a transparent oil into a white slurry. Then the slurry was filtered to yield 62 g of a white, waxy powder which was swollen with silicone oil. A sample of 10 g of the powder then was extracted with hexane and the extracted solid was dried under vacuum. A free-flowing PVP powder was obtained which weighed 2.5 g. Accordingly, the filtered polymer before extraction contained 75% of silicone oil. Its relative viscosity (it in water) evaluated using the extracted sample was 1.71 at 25° C.

EXAMPLE 2

The process of Example 1 was carried out using 360 g of the silicone oil, 36 g VP and 0.3 g Lupersol® 11, which was added in three equal portions. The reaction product was filtered yielding 140 g of a white, oily PVP polymer powder containing 75% of silicone oil.

EXAMPLE 3

Into a 1-liter, 4-necked resin kettle, fitted with an anchor agitator, a nitrogen purge adaptor, a thermometer, two subsurface feeding tubes connected with two feeding pumps, and a reflux condenser, 400 g of 5 cS silicone oil was charged. Nitrogen purging was started and continued throughout the reaction. Agitation at 200 rpm was carried out throughout the process. The reactants were heated from ambient temperature to 65° C. in 20 minutes, and held at 65° C. for 30 minutes. Then 260 microliter of t-butyl peroxypivalate (Lupersol® 11) was charged and 200 g of N-vinylpyrrolidone was charged in 6 hours while holding the temperature at 65° C. The reaction was carried out at 65° C. for a half-hour. The reaction mixture then was transferred to a 2-liter high pressure reactor and 1 g of 2,5-dimethyl-2,5-bis(t-butyl-peroxy)hexane (Lupersol® 101) was charged into the reactor. Then the reactor was sealed and heated to 120° C. and held for 8 hours. The reaction product then was cooled to room temperature.

EXAMPLE 4

The process of Example 3 was carried out using a monomer mixture of 60 g of N-vinylpyrrolidone (VP), 20 g of lauryl methacrylate and 20 g of acrylic acid separately over a period of 3 hours in place of vinylpyrrolidone alone. The reaction product was a terpolymer of VP/lauryl methacrylate/acrylic acid (60/20/20) in silicone oil.

EXAMPLE 5

The process of Example 3 was carried out using a mixture of 400 g of Carnation® light mineral oil solvent and 5 g of cetyl dimethicone copolyol (Abil® EM-90) surfactant in place of silicone oil solvent alone. The reaction product was polyvinylpyrrolidone in mineral oil solvent and cetyl dimethicone copolyol surfactant.

EXAMPLE 6

The process of Example 3 was carried out by using a monomer mixture of 60 g of vinylpyrrolidone, 20 g of lauryl methacrylate and 20 g of acrylic acid, a solvent surfactant mixture of 400 g of light mineral oil and 5 g of cetyl dimethicone copolyol (Abil® EM-90). The reaction product was a terpolymer of VP/lauryl methacrylate/acrylic acid (60/20/20) in mineral oil with surfactant.

EXAMPLE 7

The process of Example 3 was carried out by pumping a mixture of 200 g of N-vinylpyrrolidone monomer and 0.90 g of pentaerythriol triallyl ether as crosslinker and a free radical initiator in 6 hours. The reaction product was crosslinked polyvinylpyrrolidone in silicone oil.

EXAMPLE 8

The process of Example 3 was carried out using added 5 g of cetyl dimethicone copolyol (Abil® EM-90) surfactant. The reaction product was polyvinylpyrrolidone in silicone oil with surfactant present.

EXAMPLE 9

The process of Example 4 was carried out with 5 g of cetyl dimethicone copolyol (Abil® EM-90) present. The reaction product was VP/lauryl methacrylate/acrylic acid (60/20/20) terpolymer in silicone oil with surfactant present.

EXAMPLE 10

The process of Example 4 was carried out in Carnation® light mineral oil with 5 g of cetyl dimethicone copolyol (Abil® EM-90) surfactant and 0.45 g of pentaerythriol triallyl ether crosslinker present. The reaction product was crosslinked terpolymer of VP/lauryl methacrylate/acrylic acid (60/20/20) as above in mineral oil with surfactant present.

EXAMPLE 11

A mixture of 52.5 g of the filtered reaction product of Example 2 with 60 g of its filtrate added and 33 g of Dow Corning® 3225C silicone as surfactant were charged into a 1-liter vessel and homogenized to provide a uniform slurry. Homogenization was continued while 157 g of water was added dropwise over 30 min. Homogenization was continued for an additional 10 min. A uniform, white liquid emulsion was obtained having a Brookfield viscosity of 270 cPs (Spindle # 4, 20 rpm). The emulsion remained stable upon standing for 2 months; and was dilutable with silicone oil, indicating it was a water-in-oil (w/o) emulsion.

EXAMPLE 12

A 1-liter resin kettle was charged with 205 g of Dow Corning 200® Fluid silicone oil, sparged with nitrogen and heated to 65° C. Then 0.25 g of Lupersol® 11 was added. Thereafter, a mixture of 36 g of N-vinylpyrrolidone, 0.16 g of triallyl-1,3,5-triazine-2,4,6-trione (TATT) as crosslinker and 0.72 g of Span® 80 surfactant was added over 6 hours, with two additions of 0.25 g each of Lupersol® 11 after 3 and 6 hours. The reaction was continued for an additional 1 hour whereafter the reaction slurry was cooled and filtered to yield 123 g of a waxy precipitate containing about 75% silicone oil. After extraction of the silicone oil from the precipitate, the dried solid was introduced into water (a 5% by wt. solution). A gel product was obtained having a Brookfield viscosity of 2410 cps at 20 rpm.

EXAMPLE 13

The process of Example 12 was repeated using Dow Corning® 3225C as a surfactant instead of Span® 80. The product was crosslinked PVP containing about 73% silicone oil. Then 1 g of the extracted, dried polymer powder was added to 100 g water. After 24 hours at room temperature, the crosslinked polymer powder swelled into 22 ml of a gel phase.

EXAMPLE 14

A mixture of 52.5 g of the crosslinked PVP of Example 13 was homogenized with 60 g of its filtrate added and 33 g of Dow Corning® 3225C silicone surfactant. Then, continuing homogenization, 157 g of water was added dropwise over 45 minutes. Homogenization was continued for about 20 minutes using an ice bath to cool the resulting emulsion. A smooth, uniform emulsion was obtained which was similar to cosmetic face cream in consistency. Dilution with silicone oil did not change its appearance, indicating a water-in-oil (w/o) emulsion, containing crosslinked polymer in aqueous phase. The emulsion had a Brookfield viscosity of 270 cps at 20 rpm; its viscosity and appearance remained unchanged for 2 months at room temperature.

EXAMPLE 15

28 g of the filtered crosslinked PVP of Example 13 was added gradually to 133 g of an aqueous 0.5% solution of Igepal® CO-630 surfactant, under homogenization. A uniform, slightly hazy mixture was obtained to which there was added, dropwise, over 15 minutes, 39 g of Dow Corning 200® Fluid silicone oil. Homogenization was continued for an additional 30 minutes using an ice bath to cool the emulsion. A milky, viscous emulsion was obtained, which could be diluted with water, indicating an o/w emulsion. The Brookfield viscosity was 2490 cps at 20 rpm.

EXAMPLE 16

A 1-liter resin kettle was charged with 500 g of Dow Corning 200® Fluid silicone oil. The oil was sparged with nitrogen, heated to 65° C. and maintained under a nitrogen blanket. Then 10 g of silicone surfactant DC 3225C (Dow Corning) and 0.25 g Lupersol® 11 (Elf Atochem) initiator were added, and, over 6 hours, a blend of 55.75 g of N-vinylpyrrolidone, 7.72 g of Ageflex® FA-1 (N,N-dimethylaminoethyl methacrylate, a product of CPS Chemical Co.) and 19.14 g of Ageflex® FM-1Q80DMS (N,N-diethylaminoethyl methacrylate dimethyl sulfate quaternary, 80% active, a product of CPS Chemical Co.) was admitted. Hourly during this feeding of monomers, there was added 0.25 g Lupersol® 11, i.e. a total of five initiator boosters. After feeding was completed, the temperature was maintained for 2 hours. The reaction was cooled to yield a white slurry of the resultant polymer in silicone oil. The slurry was filtered to yield 197 g of a waxy powder containing 80.7 g of N-vinylpyrrolidone/N,N-dimethylaminoethyl methacrylate/N,N-dimethylamino-ethyl methacrylate diethyl sulfate quaternary terpolymer, as determined by extraction with hexane, and the remainder was silicone oil.

While the invention has been described with particular reference to certain embodiments thereof, it will be understood that changes and modifications may be made which are within the skill of the art. Accordingly, it is intended to be bound only by the following claims, in which:

What is claimed is:

1. A non-aqueous, heterogeneous polymerization process which provides a cosmetically or pharmaceutically-acceptable polymer swollen with an oil composition which comprises: polymerizing, by weight, about 5–70% of a vinyl lactam monomer wherein the vinyl monomer is a N-vinyllactam selected from N-vinyl-pyrrolidone and N-vinylcaprolactam, optionally with a comonomer selected from vinyl acetate, acrylic acid, methacrylic acid, acrylamide, methacrylamide, an alkyl (meth)acrylate, an alkyl (meth)acrylamide, a hydroxyalkyl (meth)acrylate and a hydroxyalkyl (meth)acrylamide; and a N,N-dialkylaminoalkyl (meth)acrylate and a N,N-dialkylaminoalkyl methacrylamide wherein alkyl is independently a $C_1$ to $C_4$ alkyl group, and N-quaternary derivatives thereof; and mixtures thereof, in about 30–95% of an oil as solvent, wherein said oil is selected from the group consisting of a silicone oil, a mineral oil and a water-insoluble organic ester and a free radical initiator, optionally in the presence of a crosslinking agent and/or an oil-soluble surfactant, with agitation, under an inert gas, at about 40–150° C., wherein said amount of the oil is sufficient to keep the resultant vinyl lactam polymer in a stirrable state until the end of the polymerization and wherein the vinyl monomer and optional crosslinking agent are fed into the reactor charged with said oil and free radical initiator continuously over a period of about 3–6 hours at a rate such that substantially no free monomer is present during the polymerization.

2. A process according to claim 1 in which the oil soluble surfactant is present.

3. A process according to claim 1 which includes about 0.1–10 wt. % of a crosslinking agent, based on the amount of vinyl monomer present.

4. A process according to claim 3 wherein said crosslinking agent is present in an amount of 0.3–2%.

5. A process according to claim 1 wherein the vinyl lactam monomer is N-vinylpyrrolidone.

6. A process according to claim 1 wherein the crosslinking agent is diallylimidazolidone, divinyl ether of diethylene glycol, pentaerythritol triallyl ether (PETA); triallyl-1,3,5-triazine-2,4,6-(1H,3H,5H)trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis (methacrylamide), methylene-bis (acrylamide), N,N-divinylimidazolidone, ethylidene-bis (N-vinyl-pyrrolidone) (EBVP), hexaallyl sucrose, or bis (N,N-acrylamide).

7. A process according to claim 6 wherein the vinyl lactam monomer is N-vinylpyrrolidone.

8. A process according to claim 1 wherein the free radical initiator is diacetyl peroxide, dibenzoyl peroxide, dilauroyl peroxide, t-butyl peroxypivalate, t-amyl peroxypivalate, t-butyl peroxy-2-ethyl-hexanoate; di-(4-tert-butylcyclohexyl) peroxydicarbonate, 2,2'-azo-bis (isobutyrolnitrile), 2,2'-azo-bis(2,4-dimethylvaleronitrile), or 1,1'-azo-bis (cyanocyclo-hexane), and mixtures thereof.

* * * * *